US009604019B2

(12) United States Patent
Altobelli et al.

(10) Patent No.: US 9,604,019 B2
(45) Date of Patent: Mar. 28, 2017

(54) DETECTION SYSTEM AND METHOD FOR AEROSOL DELIVERY

(71) Applicant: DEKA Products Limited Partnership, Manchester, NH (US)

(72) Inventors: David E. Altobelli, Hollis, NH (US); Larry B. Gray, Merrimack, NH (US); Derek G. Kane, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 14/229,116

(22) Filed: Mar. 28, 2014

(65) Prior Publication Data

US 2014/0209094 A1  Jul. 31, 2014

Related U.S. Application Data

(63) Continuation of application No. 12/964,205, filed on Dec. 9, 2010, now Pat. No. 8,687,191, which is a continuation of application No. 12/437,306, filed on May 7, 2009, now abandoned, which is a continuation of application No. 12/045,386, filed on Mar. 10, (Continued)

(51) Int. Cl.
| | |
|---|---|
| *G01N 21/00* | (2006.01) |
| *A61M 15/00* | (2006.01) |
| *A61B 5/08* | (2006.01) |
| *G01N 15/02* | (2006.01) |
| *G01N 15/14* | (2006.01) |
| *G01N 21/53* | (2006.01) |
| *G01F 1/34* | (2006.01) |
| *A61M 16/00* | (2006.01) |

(Continued)

(52) U.S. Cl.
CPC ........... *A61M 15/009* (2013.01); *A61B 5/08* (2013.01); *A61M 15/0065* (2013.01); *G01F 1/34* (2013.01); *G01N 15/02* (2013.01); *G01N 15/0205* (2013.01); *G01N 15/1456* (2013.01); *G01N 21/53* (2013.01); *A61M 2016/0021* (2013.01); *A61M 2016/0039* (2013.01); *A61M 2205/3306* (2013.01); *G01N 2001/2223* (2013.01); *G01N 2021/4707* (2013.01)

(58) Field of Classification Search
CPC ....................... G01N 21/00; G01N 2001/2223
USPC ........................................................ 356/338
See application file for complete search history.

(56) References Cited

U.S. PATENT DOCUMENTS 4,489,863 A * 12/1984 Horchos ............... F16K 31/082
                                                              222/504
4,589,280 A *  5/1986 Carter .................... A61B 5/201
                                                              600/573

(Continued)

*Primary Examiner* — Roy M Punnoose
(74) *Attorney, Agent, or Firm* — Michelle Saquet Temple

(57) ABSTRACT

An apparatus comprises a detector, a pressure sensor and a processor. The detector is operable to detect light that is scattered by an aerosol that is associated with a pressure. The pressure sensor is operable to measure the pressure. The processor is coupled to the detector and to the pressure sensor, and is configured to receive at least a signal from the detector and the pressure sensor. The processor is further configured to use the received signals to calculate a volume of the first aerosol, and to output an output signal associated with the calculated volume. The various measurements can be repeated and compared, and the output signal can be a feedback signal for metering subsequent amounts of the aerosol, based on the comparison.

14 Claims, 7 Drawing Sheets

Related U.S. Application Data 2008, now Pat. No. 7,548,314, which is a continuation of application No. 10/675,278, filed on Sep. 30, 2003, now Pat. No. 7,342,660, which is a continuation-in-part of application No. 10/670,655, filed on Sep. 25, 2003, now abandoned.

(51) Int. Cl.
  *G01N 1/22* (2006.01)
  *G01N 21/47* (2006.01)

(56) References Cited

U.S. PATENT DOCUMENTS

| | | | | |
|---|---|---|---|---|
| 4,683,748 A * | 8/1987 | Carter | A61B 5/201 | 600/573 |
| 4,819,629 A * | 4/1989 | Jonson | A61M 15/00 | 128/200.14 |
| 5,363,842 A * | 11/1994 | Mishelevich | A61B 8/0875 | 128/200.14 |
| 5,392,768 A * | 2/1995 | Johansson | A61M 15/00 | 128/200.14 |
| 5,626,131 A * | 5/1997 | Chua | A61M 16/00 | 128/204.23 |
| 5,887,586 A * | 3/1999 | Dahlback | A61B 5/083 | 128/203.12 |
| 6,089,229 A * | 7/2000 | Bathe | A61M 16/12 | 128/203.12 |
| 6,305,212 B1 * | 10/2001 | Drzewiecki | A61M 16/0051 | 422/82 |
| 6,390,091 B1 * | 5/2002 | Banner | A61M 16/0051 | 128/202.22 |
| 6,467,477 B1 * | 10/2002 | Frank | A61M 16/00 | 128/203.23 |
| 6,644,311 B1 * | 11/2003 | Truitt | A61M 16/00 | 128/204.18 |
| 7,724,150 B2 * | 5/2010 | Chandler | G01N 15/0205 | 340/627 |
| 2009/0058668 A1 * | 3/2009 | Chandler | G01N 15/0205 | 340/627 |

\* cited by examiner

FIG. 1

AEROSOL SELECTOR 101

ATOMIZER 102

LIGHT SOURCE 104

DETECTOR 105

PROCESSOR 106

VARIABLE RESISTANCE REGION 108

PRESSURE SENSOR 107

FIXED RESISTANCE REGION 109

103 — AEROSOL FLOW PATH

```
INITIAL CONDITIONS
       501
         │
         ▼
- INHALE/ SETUP
  ◇ PRESSURE GAUGE CHANGES
  ◇ LUNGS EXPAND
       502
         │
         ▼
- BREATH HOLD / METERING
  ◇ VALVE OPENS
  ◇ FLUID IS DELIVERED TO ATOMIZER
  ◇ FLUID IS METERED
       503
         │
         ▼
- EXHALE
  ◇ PRESSURE GAUGE INDICATES AIR FLOW
  ◇ LASER IS ACTIVE
       504
         │
         ▼
- INHALE
  ◇ PRESSURE GAUGE INDICATES AIR FLOW
  ◇ AIR VALVE OPENS
  ◇ TARGET VOLUME IS ATOMIZED
  ◇ LASER ACTIVATES
  ◇ AEROSOL VOLUME IS CALCULATED
       505
         │
         ▼
- BREATH HOLD
  ◇ PRESSURE GAUGE INDICATES AIR FLOW
       506
         │
         ▼
- EXHALE
  ◇ PRESSURE GAUGE INDICATES AIR FLOW
  ◇ LASER ACTIVATES
  ◇ AEROSOL VOLUME IS CALCULATED
       507
         │
         ▼
- TARGET VOLUME IS ADJUSTED
       508
         │
         ▼
SEQUENCE IS REPEATED
       509
```

FIG. 5

DETECTION SYSTEM AND METHOD FOR AEROSOL DELIVERY

CROSS REFERENCE TO RELATED APPLICATIONS

This application is a continuation of U.S. patent application Ser. No. 12/964,205, filed Dec. 9, 2010, and entitled "Detection System and Method for Aerosol Delivery", now U.S. Pat. No. 8,687,191, issued Apr. 1, 2014, which is a continuation application of U.S. patent application Ser. No. 12/437,306, filed May 7, 2009, and entitled "Detection System and Method for Aerosol Delivery" now abandoned, which is a continuation of U.S. patent application Ser. No. 12/045,386, filed Mar. 10, 2008, and entitled "Detection system and Method for Aerosol Delivery", now U.S. Pat. No. 7,548,314 issued Jun. 16, 2009, which is a continuation of U.S. patent application Ser. No. 10/675,278, filed Sep. 30, 2003, and entitled "Detection System and Method for Aerosol Delivery", now U.S. Pat. No. 7,342,660 issued Mar. 11, 2008, which is a continuation-in-part of U.S. patent application Ser. No. 10/670,655, filed Sep. 25, 2003, and entitled "Detection System and Method for Aerosol Delivery", now abandoned, all of which are incorporated herein by reference in their entireties.

NOTICE OF COPYRIGHT PROTECTION

A section of the disclosure of this patent document contains material subject to copyright protection. The copyright owner has no objection to the facsimile reproduction by anyone of the patent document, but otherwise reserves all copyright rights whatsoever.

TECHNICAL FIELD

The present invention generally relates to systems and methods for measuring quantities of aerosolized compounds. More particularly, embodiments of the present invention can relate to systems and methods for accurately delivering atomized substances, such as therapeutic agents.

BACKGROUND INFORMATION

A variety of substances, such as therapeutic agents, may be delivered by inhalation, including aerosolized liquids and powder drugs, for the therapeutic treatment of the lungs and inhalation passageways and/or for the delivery of systemic agents. The inhalation of systemic therapeutic agents is considered a potential alternative to injections and other types of drug delivery systems. For example, insulin may be delivered by inhalation in aerosolized form, thus avoiding the need for the injection of insulin into a patient, Inhaling aerosols, however, typically lacks the accuracy of injections, and so may be inappropriate for use in situations where accurate dosing is critical with aerosolized drugs, the proper amount; required for delivery is often not properly metered for delivery. For example, asthma inhalers typically have an acceptable accuracy of plus or minus 25% of the nominal dose. For systemic drug delivery of insulin, cm the other hand, such a level of accuracy is considered too unpredictable to allow for appropriate use, even though aerosolized delivery may be preferable to intravenous delivery for a variety of reasons.

Thus, a need exists for accurately and predictably delivering a predetermined dose of aerosolized drugs.

SUMMARY

An embodiment comprises a light detector, a pressure sensor and a processor. The light detector is operable to detect light that is scattered by an aerosol that is associated with a pressure. The pressure sensor is operable to measure the pressure. The processor is coupled to the light detector and to the pressure sensor, and is configured to receive at least a signal from the detector and the pressure sensor. The processor is further configured to use the received signals to calculate a volume of the first aerosol, and to output, a signal associated with the calculated volume.

BRIEF DESCRIPTION OF THE DRAWINGS

FIG. 1 is a schematic diagram of a system for delivering aerosol according to an embodiment of the invention.

FIG. 5 is a block diagram of a method of measuring the physical characteristics of an aerosol according to an embodiment of the invention.

DETAILED DESCRIPTION

Figure 2:
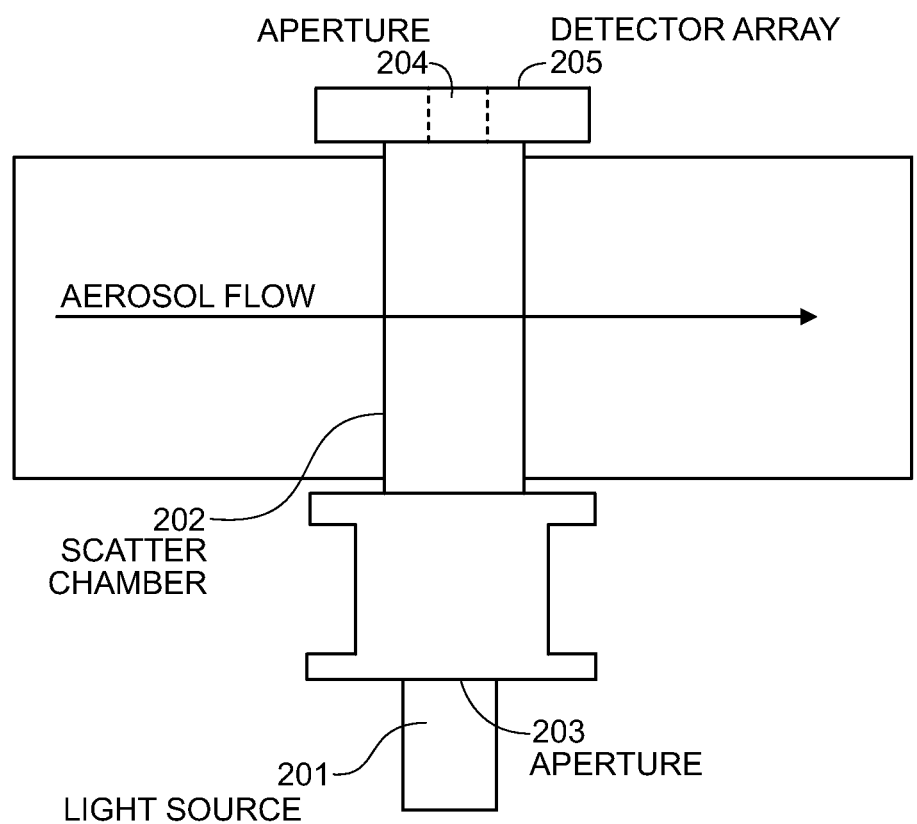
FIG. 2 is a block diagram of a light scatter detector according to an embodiment of the invention.

Embodiments of the invention include systems and methods for measuring, analyzing, and metering aerosols. For purposes of this application, the term aerosol includes airflows containing particles, such as aerosolized liquids, powders, and combinations of these, as well as airflows that do not contain any aerosolized particles. One use for the invention is as a real time aerosol volume transducer. With this use, aerosol density (for example, aerosol particles per liter) in a system can be measured by light scatter. If airflow (for example, liters per second) is also determined, then these two parameters multiplied together yield the number of aerosol particles per second passing through the chamber. The number of particles per second can then be integrated to calculate the total number of aerosol particles (i.e. volume) that passed through the system. The volume measurement can be repeated, and a comparison of volume measurements can be fed back to a system to, for example, meter subsequent amounts of aerosol.

FIG. 1 shows a block diagram of a contextual overview for employing embodiments of the present invention. In this overview, a substance, which can be a liquid or solid form of a therapeutic agent, or which can be any liquid or solid capable of being converted to an aerosol, is contained in aerosol selector 101. Aerosol selector 101 includes atomizer 102, and is coupled to aerosol flow path 103 such that an aerosol can be introduced from atomizer 102 into aerosol flow path 103. For purposes of the application, the term atomizer includes any devise or component that is capable of producing an aerosol from solids, liquids, or any combination thereof.

In one embodiment of the invention, aerosol flow path 103 includes a light source 104, a light detector 105 and a pressure sensor 107. Light detector 105 and pressure sensor 107 are coupled to processor 106. Processor 106 can be configured to receive a signal from light detector 105 and a signal from pressure sensor 107. The respective signals can be sent to processor 106 in substantially real time, or in some way that associates the respective signals.

Processor 106 can be further configured to calculate a volume of the first aerosol, the calculation being based on the signal received from light detector 105 and on the signal received from pressure sensor 107. In one embodiment, processor 106 can calculate aerosol volume by receiving a signal from detector 105 that is associated with aerosol density, receiving a signal from pressure sensor 107 that is associated with pressure or flow rate, and multiplying the aerosol density (i.e., number of particles per unit volume) by the pressure or flow rate. The result is a representation of the number of particles per second that traverses aerosol flow path 103, or that traverses some subvolume of aerosol flow path 103. The number of particles per second can then be integrated over time to calculate the total number of aerosol particles (i.e. volume) that passed through the system.

Alternatively, airflow can be measured in a variety of way other than utilizing pressure sensor 107. For example, airflow can be measured by a turbine-type meter or a hot-wire anemometer.

In one embodiment, processor 106 can be configured to repeat the volume calculation for aerosols that are subsequently introduced into aerosol flow path 103, and compare previous and subsequent volume calculations. The comparison can be used to create a feedback signal, output from processor 106 and received by aerosol selector 101, for metering subsequent aerosols.

In another embodiment, processor 106 is configured to receive a first signal and a second signal from light detector 105. The first signal is associated with light scattering from a first aerosol that is associated with a first pressure. For the purposes of the invention, the phrase "first aerosol" means an aerosol with distinct properties such as composition, number of particles per unit volume, and particle size. The second signal is associated with light scattering from a second aerosol that is associated with a second pressure. For the purposes of the invention, the phrase "second aerosol" means an aerosol with a number of particles per unit volume, a particle size or a general composition that may or may not be different from the first aerosol.

One skilled in the art will understand that the first pressure and the second pressure may or may not be the same pressure, and may or may not occur in the same region, or in different regions that have the same general geometry.

In one embodiment, the first aerosol is a medicine to be inhaled, the first pressure is associated with inhalation, and the second pressure is associated with exhalation. In other embodiments, the first and second pressures can be from sources not associated with inhalation and exhalation. Processor 106 is further configured to output an output signal associated with a comparison of the first signal and the second signal. For the purposes of the invention, the term "comparison" may include any measure of difference between the first aerosol and the second aerosol. For example, the comparison may include subtracting the number of particles per unit volume in the first aerosol from the number of particles per unit volume in the second aerosol. Alternatively, the comparison may include, for example, determining the ratio of such numbers of particles, or comparing input particle size to output particle size. In one embodiment, breath pause timing can be measured.

The output signal can be fed back to aerosol selector 101 to improve, refine, or otherwise assist in any function performed by aerosol selector 101. In addition, the output signal can be used to alter the user's flow pattern for optimal deposition. For example, the output signal can contain information used to indicate to a patient to breath longer, deeper, shorter and/or shallower.

In one embodiment, aerosol selector 101 can receive the output signal, and can use the information contained in the output signal to meter a third aerosol. For the purposes of the invention, the term "third aerosol" means an aerosol with a number of particles per unit volume, a particle size, or a general composition that may or may not be different from the first aerosol. In another embodiment, the output signal can include comparison information to assist in metering subsequent doses such that the total dose delivered to a patient can be delivered in predictable and/or measurable quantities.

Light source 104 can be a laser, or any light source that is practicable for the present invention. For example, light source 104 can be a light emitting diode (with or without a collimator), or can be a fluorescence of the aerosol itself. Light from light source 104 can be polarized and/or collimated in such a way that, after scattering from the aerosol, the light can be detected in detector 105. Light detector 105 can be any light detector, or multiple light detectors, or an array of light detectors, or any combination of light detectors in any geometry operable to detect scattered light, and to send a signal to processor 105. For example, light detector 105 can be any practicable number and combination of photomultiplier tubes, CCDs, silicon photodetectors, pyroelectric detectors, etc. Examples of appropriate geometries include concentric circles, grid patterns, or any geometry practicable for the purposes of a particular measurement. For the purposes of the present invention, the term "scatter" includes, but is not limited to, scattering due to diffraction.

For the purposes of the invention, the term processor includes, for example, any combination of hardware, computer programs, software, firmware and digital logical processors capable of processing input, executing algorithms, and generating output as necessary to practice embodiments of the present invention. Such a processor may include a microprocessor, an Application Specific Integrated Circuit (ASIC), and state machines. Such a processor can include, or can be in communication with, a processor readable medium that stores instructions that, when executed by the processor, causes the processor to perform the steps described herein as carried out, or assisted, by a processor.

For the purposes of the invention, "processor readable medium," or simply "medium," includes but is not limited to, electronic, optical, magnetic, or other storage or transmission devices capable of providing a processor with processor readable instructions. Other examples of suitable media include, but are not limited to, a floppy disk, CD-ROM, magnetic disk, memory chip, ROM, RAM, ASIC, configured processor, all optical media, all magnetic tape or other magnetic media, or any other medium from which a processor can read. Also, various other forms of processor readable media may transmit or carry instructions to a computer, including a router, private or public network, or other transmission device or channel. Also, various other forms of processor readable media may transmit or carry instructions to a computer, including a router, private or public network, or other transmission device or channel.

Aerosol flow path 103 can further include a region of variable pressure resistance 108, and a region of fixed pressure resistance 109.

FIG. 2 shows a block diagram of a light scatter detector according to an embodiment of the invention. In this embodiment, light source 201 is coupled to scatter chamber 202 by aperture 203. Light source 201 can be, for example, a laser diode emitting a laser beam. Aperture 203 is configured to remove stray light emitted by the laser diode, and has a length that provides room for properly focusing the laser beam within scatter chamber 202. The laser beam can exit the chamber through aperture 204 in light detector 205.

When light passes through the aerosol, the light can scatter away from the optical path. Accordingly, scatter chamber 202 can be a polished aluminum tube, or can be any material that allows scattered light to be directed toward light detector 205.

Because air and vapor do not scatter as much light as an aerosol, the amount of light scattered depends largely on the density of the aerosolized particles in the light path. Thus, knowledge of the airflow rate, provided by a pressure sensor, and the amount of light scattered from a laser beam, allows the mass flow of aerosol to be determined. Ideally, the amount of light scattered by a monodispersed aerosol is represented by the following equation:

$$I_m = I_0(1 - e^{-\alpha \cdot \rho \cdot ho}) + I_{DC}.$$

In this equation, the variables $I_m$, $I_0$, and $I_{DC}$ are the measured intensity, the incident intensity, and the background intensity. The variable $\alpha$, with units of $m^3$, is a coefficient converting the density of scatterers, $\rho$, having units of #scatterers/$m^3$, into the probability that a photon will pass through the chamber without scattering. The coefficient $\alpha$ is essentially independent of all factors except for physical characteristics of the aerosol and the geometry of the chamber. When the aerosol is sufficiently similar to the calibration standard, the measured intensity only depends upon the amount of incident light, the background light, and the density of scatters.

Again ideally, the density of scatterers is given by $\rho = \gamma \cdot (\mu_m/Q)$, where $\mu_m$ is the volume flow rate of the aerosolized particles $\mu L/s$, Q is the volume flow rate of air, L/s, and $\gamma$ is a coefficient relating mass of the aerosolized particles to the number of scattering particles. The coefficient $\gamma$ has units of $L/\mu L m^3$.

To solve for $\mu_m$, $\mu_m = (-Q/\alpha \cdot \gamma)[\ln(I_0 + I_{DC} - I_m) - \ln(I_0)]$. This equation provides a nominal functional relation between aerosol mass flow, airflow, and measured intensity. In practice, of course, embodiments of the system exhibit non-ideal and non-linear behavior. These behaviors can be based on (i) a non-zero width of the laser beam; (ii) a non-constant velocity profile of the airflow and aerosol distribution; (iii) a polydispersed aerosol; and (iv) volatility of the aerosol.

Thus, the volume flow rate of the aerosolized particles may retain the form $\mu_m = f(Q\{\ln(I_0 + I_{DC} - I_m) - \ln(I_0)\})$. To accommodate for non-linearities, the following cubic approximation to the true functional relation may be used: $1m = i = 13 a_i \{Q[\ln(I_0 + I_{DC} - I_m) - \ln(I_0)]\}^i$.

This relation and its coefficients absorb the product $\alpha \cdot \gamma$.

The coefficients $a_i$ can be determined in a number of ways, including through the use of a standard least-squares algorithm to minimize the difference between predicted mass flow and mass flow measured from a calibrated aerosol or a test strip with a calibration scattering coefficient.

In one embodiment, light source 201 can be modulated with an on-off square beam to improve the signal to noise ratio. In this embodiment, the detector signal is integrated during the on period, $S_1$, and separately during the off period, $S_0$. The signal used to calculate aerosol volume is thus the difference, $S_1 - S_0$. To implement this embodiment, the system is configured such that the baseline noise from the detector and any ambient light are likely captured by the off-period signal. In other embodiments of the invention, other modulation techniques can be used to improve the signal to noise ratio.

Figure 2A:
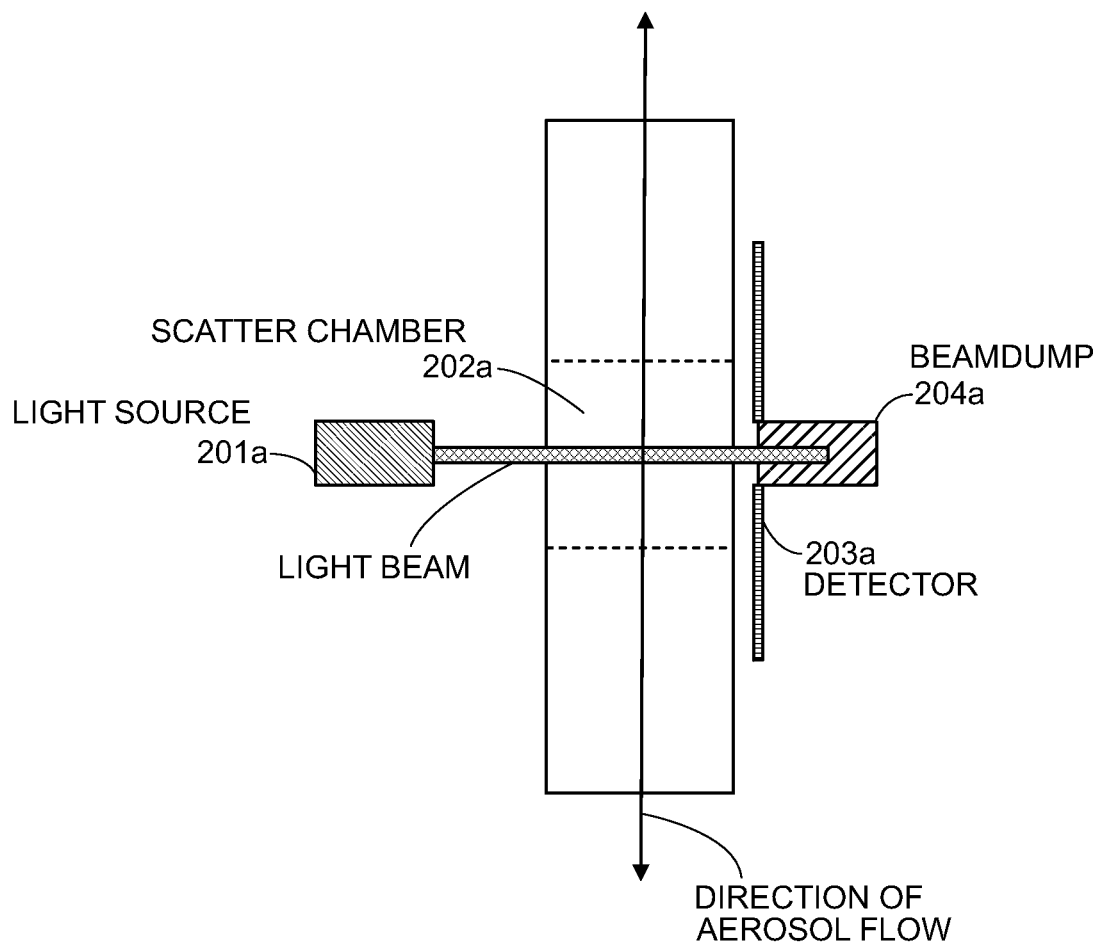
FIG. 2A is a block diagram of a light scatter detector including a beam dump, according to an embodiment of the invention.

FIG. 2A is a block diagram of a light scatter detector including a beam dump according to an embodiment of the invention. In this embodiment, light source 201a emits light into scatter chamber 202a. Detector 203a contains an aperture (not numbered), so that when light from light source 201a exits the aperture, it illuminates beam dump 204a. Beam dump 204a is in the direct path of the light beam, and is configured to absorb or contain light that is not scattered by the aerosol. In one embodiment, beam dump 204a is simply a hole allowing the light beam to exit the system.

Figure 3:
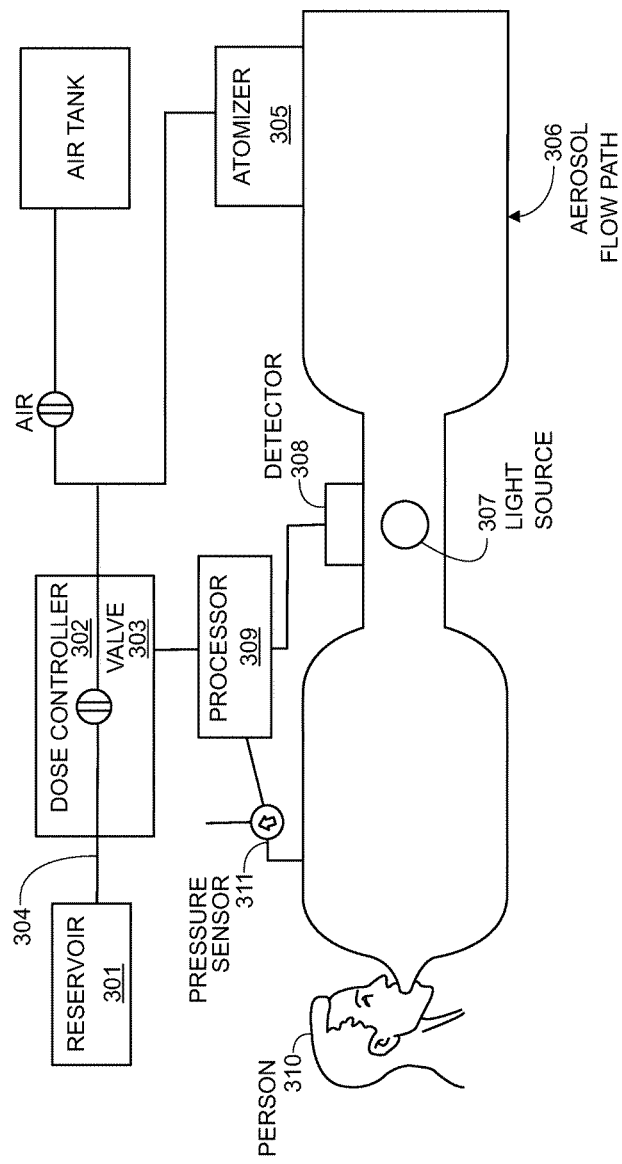
FIG. 3 is a schematic diagram of a system for delivering aerosol according to an embodiment of the invention.

FIG. 3 is a schematic diagram of a system for delivering an aerosol according to an embodiment of the invention. The context for the embodiment displayed in this figure is a device capable of delivering doses of aerosolized drugs. In this embodiment, reservoir 301 is coupled to dose controller 302 via flow channel 304. Dose controller 302, including valve 303, is configured to deliver a metered amount of the compound to atomizer 305 via flow channel 306. Atomizer 305, upon receiving the compound, can create an aerosol of the compound and deliver it to flow path 306, which can be a user interface, or it can be any type of conduit for the aerosol.

In one embodiment, aerosol flow path 306 includes light source 307 and light detector 308. Light source 307 is configured to send light across aerosol flow path 306, either directly or in combination with mirrors and collimators, or in any practicable way such that scattered light can be detected by light detector 308. Light detector 308 is placed in such a way that it can detect light from light source 307, including light that has scattered from an aerosol present in aerosol pathway 306. Processor 309, coupled to light detector 308, is further coupled to dose controller 302 and can provide a signal to dose controller 302 that is associated with the light detected at light detector 308.

In one embodiment, aerosol flow path 306 includes pressure sensor 311 for detecting pressure inside aerosol flow path 306. Pressure sensor 311 can be coupled to processor 309. In this embodiment, processor 309 can use information received from pressure sensor 311 in providing an output signal for feedback to dose controller 302.

In one embodiment, person 310 can receive the aerosol by inserting the distal end of aerosol flow path 306 into an orifice, and inhaling the aerosol. After delivering the aerosol to person 310, processor 309 is configured to receive a signal from light detector 310 and send an output signal to dose controller 302. The output signal can include information for metering a subsequent dose or doses.

In another embodiment of the invention, processor 309 is configured to receive a signal from light detector 308 that is associated with person 310 exhaling after inhaling the aerosol. Using the signal associated with inhaling and the signal associated with exhaling, processor 309 is configured to calculate a comparison of the two signals, and send an output signal associated with this comparison to dose controller 302. The output signal can include information for metering a subsequent dose or doses.

Figure 4:
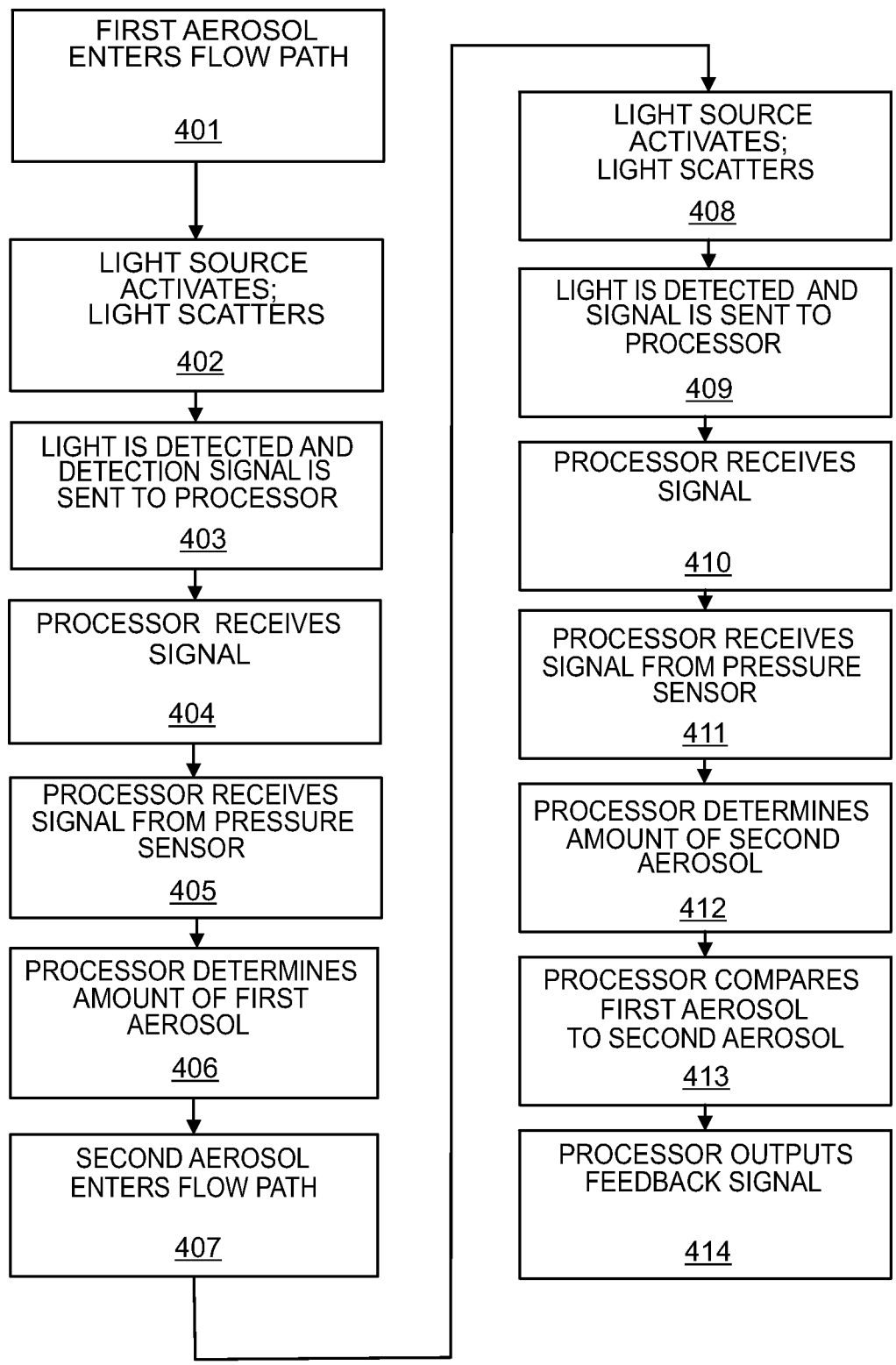
FIG. 4 is a block-diagram of a method of measuring the physical characteristics of an aerosol according to an embodiment of the invention.
Figure 6:
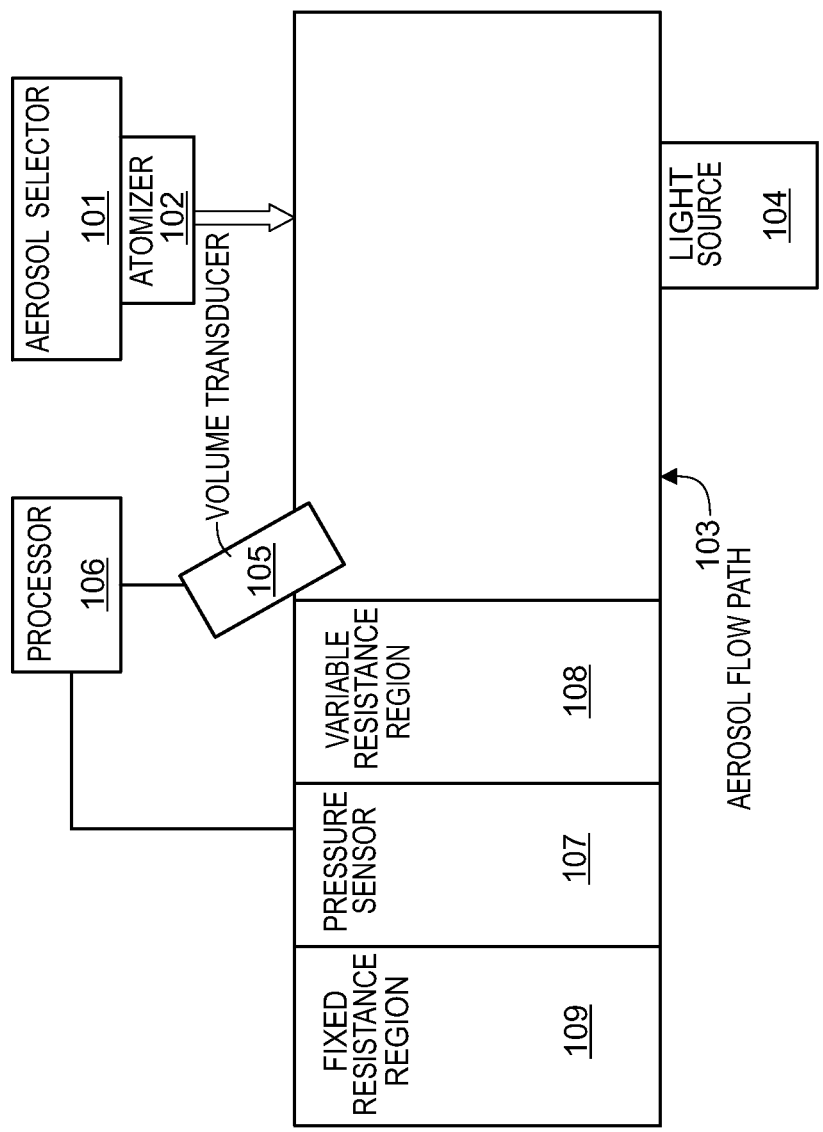
FIG. 6 is a schematic diagram of a system for delivering aerosol according to an embodiment of the invention.

FIG. 4 is a block-diagram overview of a method according to an embodiment of the invention. One skilled in the art will recognize that the steps described in FIG. 4 need not necessarily be performed in the order displayed; the steps may be performed in any order practicable.

At step 401, a first aerosol enters a flow path under a first pressure. The first pressure can be caused by, for example, inhalation, exhalation, or any other practicable source for creating pressure appropriate for a given context. At step 402, a light source activates and light from the light source scatters from a first aerosol. One skilled in the art would understand that the light source may not be a single light source, but can be any appropriate combination of light sources.

At step 403, a light detector detects the scattered light, and sends a light-detection signal to a processor to process the signal. At step 404, the processor receives the light-detection signal.

At step 405, the processor receives from a pressure sensor a signal associated with the airflow, or any general fluid flow, in the flow path. The processor, at step 406, can use the received signals to calculate the amount of the first aerosol that traverses the flow path.

At step 407, a second aerosol enters the flow path under a second pressure. The second pressure can be caused by, for example, inhalation, exhalation, or any other practicable source for creating a pressure appropriate for a given context. The light source is activated at step 408, and light from the light source is scattered from the second aerosol.

Next, at step 409, the scattered light is detected by the light detector, and a detection signal is sent to the processor for processing. The signal is received by the processor at step 410, and at step 411, the processor receives a signal from the pressure sensor associated with the aerosol flow in the flow path.

The processor, at step 412, can use the received signals to calculate the amount of the second aerosol that traverses the flow path. At step 413, the processor compares the amount of the first aerosol detected with the amount of the second aerosol detected, and outputs a signal associated with the difference between the two at step 414.

FIG. 5 is a block diagram of a method according to an embodiment of the invention. This method is presented in the context of a person inhaling and exhaling an aerosolized drug. One skilled in the art will recognize, however, that the method is equally applicable in any situation in which a compound is metered, aerosolized and dispensed under pressure. One skilled in the art will further recognize that the steps described in FIG. 4 need not necessarily be performed in the order displayed; the steps may be performed in any order practicable.

At step 501, initial conditions for depositing the aerosol are set up. In these initial conditions, the compound to be aerosolized exists in a reservoir chamber. At this point, the system metering valve is closed, and the light source and light detector for measuring the deposited dose are dormant.

At step 502, a person's lungs expand, thereby creating a pressure region in the aerosol flow path. A pressure sensor changes in response to this change in pressure.

At step 503, the person holds his breath and the drug is metered by a dose controller. At this point, a valve opens, delivering the drug to an atomizer. At step 504, the person exhales, and the pressure sensor reflects this change in pressure. At this point, light source is active. One skilled in the art will appreciate that steps 502 and 503 can be used to calibrate the system by creating a baseline measurement that can be subtracted out of subsequent aerosol measurements.

Possible methods of metering include, but are not limited to, using a piston or syringe device, a peristaltic pump. Other possible methods include using acoustic volume sensing (AVS) techniques as described in U.S. Pat. No. 5,575,310, incorporated herein in its entirety, and fluid management system (FMS) techniques as described in U.S. Pat. No. 5,193,990, incorporated herein in its entirety.

The aerosol is delivered to the person in step 505. In this step, the person inhales. The change in pressure is noted by the pressure sensor, and an air valve opens. In this step, the target volume is atomized at an atomizer, and the aerosol flows into an aerosol flow path for measurement and delivery to the person. The light source is active in this step, the pressure sensor indicates pressure, and the aerosol volume of the inhaled aerosol is calculated. In one embodiment, the aerosol is delivered at room temperature. In this step, the person can hold his breath to maximize aerosol deposition in the lungs.

At step 507, the person exhales, causing the pressure sensor to indicate airflow. At this step, the light source is activated and the aerosol volume of the exhaled aerosol is calculated. Using the calculations performed during inhalation and exhalation, at step 508, the target volume of the aerosol is adjusted. At step 509, the sequence is repeated.

In one embodiment of the invention, the method steps of FIG. 5 are embodied as a computer program on a processor readable medium that stores instructions to cause a processor to perform the steps of the method.

The foregoing description of the embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the present invention.

What is claimed is:

1. An apparatus comprising:
a sensor operable to determine a pressure; and
a processor coupled to the sensor, the processor configured to:
  receive a signal associated with the sensor that is associated with a first therapeutic agent introduced into a flow path;
  calculate a volume of the first therapeutic agent when the processor receives a signal associated with the sensor, the calculation based on the signal representing the sensor;
  receive a signal associated with the sensor from a second therapeutic agent introduced into a flow path;
  calculate a volume of the second therapeutic agent when the processor receives a signal associated with the sensor, the calculation based on the signal representing the sensor; and
  output a signal associated with a comparison of the volume of the first therapeutic agent and the volume of the second therapeutic agent.

2. The apparatus of claim 1, further comprising dose-selection means coupled to the processor, and wherein the output signal is received by the dose-selection means, and wherein the output signal includes information useful for metering a third therapeutic agent.

3. The apparatus of claim 1, wherein the output signal comprising information for metering a third therapeutic agent.

4. The apparatus of claim 1, further comprising a light source located within the flow path.

5. The apparatus of claim 4, further comprising a detector operable to detect light.

6. An apparatus comprising:
a sensor operable to determine a pressure;
a light source located within a flow path; and
a processor coupled to the sensor, the processor configured to:
receive a signal associated with the sensor that is associated with a first therapeutic agent introduced into the flow path;
calculate a volume of the first therapeutic agent when the processor receives a signal associated with the sensor, the calculation based on the signal representing the sensor;
receive a signal associated with the sensor from a second therapeutic agent introduced into a flow path;
calculate a volume of the second therapeutic agent when the processor receives a signal associated with the sensor, the calculation based on the signal representing the sensor; and
output a signal associated with a comparison of the volume of the first therapeutic agent and the volume of the second therapeutic agent.

7. The apparatus of claim 6, further comprising a detector operable to detect light.

8. The apparatus of claim 6, further comprising dose-selection means coupled to the processor, and wherein the output signal is received by the dose-selection means, and wherein the output signal includes information useful for metering a third therapeutic agent.

9. The apparatus of claim 6, wherein the output signal comprising information for metering a third therapeutic agent.

10. An apparatus comprising:
a sensor operable to determine a pressure; and
a processor coupled to the sensor, the processor configured to:
receive a signal associated with the sensor that is associated with a first therapeutic agent introduced into a flow path;
calculate a volume of the first therapeutic agent when the processor receives a signal associated with the sensor, the calculation based on the signal representing the sensor;
receive a signal associated with the sensor from a second therapeutic agent introduced into a flow path;
calculate a volume of the second therapeutic agent when the processor receives a signal associated with the sensor, the calculation based on the signal representing the sensor; and
output a signal associated with a comparison of the volume of the first therapeutic agent and the volume of the second therapeutic agent.

11. The apparatus of claim 10, further comprising a light source located within the flow path.

12. The apparatus of claim 11, further comprising a detector operable to detect light.

13. The apparatus of claim 10, further comprising dose-selection means coupled to the processor, and wherein the output signal is received by the dose-selection means, and wherein the output signal includes information useful for metering a third therapeutic agent.

14. The apparatus of claim 10, wherein the output signal comprising information for metering a third therapeutic agent.

* * * * *